United States Patent
Prieur et al.

(10) Patent No.: US 6,605,467 B2
(45) Date of Patent: *Aug. 12, 2003

(54) FUSION PROTEIN COMPRISING THE WHOLE OR PART OF THE PP65 PROTEIN OF HUMAN CMV, USEABLE IN PARTICULAR FOR PREPARING A VACCINE

(75) Inventors: Eric Prieur, Headington (FR); Jacqueline Lule, Plaisance du Touch (FR); Jean-Luc Davignon, Tournefeuille (FR); Christian Davrinche, Cornebarrieu (FR)

(73) Assignee: Institut National de la Sante et de la Recherche Medicale (INSERM), Paris (FR)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/319,264
(22) PCT Filed: Dec. 12, 1997
(86) PCT No.: PCT/FR97/02285
§ 371 (c)(1),
(2), (4) Date: Jul. 6, 1999
(87) PCT Pub. No.: WO98/26074
PCT Pub. Date: Jun. 18, 1998

(65) Prior Publication Data
US 2002/156251 A1 Oct. 24, 2002

(30) Foreign Application Priority Data
Dec. 13, 1996 (FR) .......................................... 96 15344

(51) Int. Cl.[7] .......................... C12N 5/00; C12N 15/36; C12N 15/62; C07K 19/00; C07K 14/045
(52) U.S. Cl. ...................... 435/377; 435/375; 536/23.4; 536/23.72; 530/350
(58) Field of Search .......................... 530/350, 324–326; 435/235.1, 69.1, 69.3, 69.7, 377, 375; 536/23.4, 23.72

(56) References Cited

U.S. PATENT DOCUMENTS

| 5,800,981 | A | * | 9/1998 | Bruggeman et al. | ............ 435/5 |
| 6,120,989 | A | * | 9/2000 | Vornhagen et al. | ............ 435/5 |
| 6,342,226 | B1 | * | 1/2002 | Betberder et al. | ...... 424/196.11 |

FOREIGN PATENT DOCUMENTS

| DE | 44 26 453 | * | 11/1995 | ........... C07K/14/08 |
| WO | 94/00150 | | 1/1994 | |
| WO | 96/01321 | | 1/1996 | |
| WO | 96/06638 | * | 3/1996 | .......... A61K/39/39 |
| WO | 96/39491 | | 12/1996 | |
| WO | 97/31117 | | 8/1997 | |
| WO | 98/26074 | * | 6/1998 | ........... C12N/15/38 |

OTHER PUBLICATIONS

Wills et al (Journal of Virology 70(11): 7569–7579, Nov. 1996).*
Del Val et al (Journal of Virology 65(7): 3641–3646, 1991).*
van Zanten et al (Journal of Infectious Diseases 172:879–82, 1995).*
van Zanten et al (Clinical and Diagnostic Laboratory Immunology 2(2): 214–218, 1995).*
Beninga et al (Journal of General Virology 76:153–160, 1995).*

* cited by examiner

Primary Examiner—Mary E. Mosher
(74) Attorney, Agent, or Firm—Foley & Lardner (57) ABSTRACT

The invention concerns a fusion protein characterised in that it comprises at least part of the pp65 protein of the cytomegalovirus (or CMV), or a protein having at least 80% homology with the pp65 protein, in combination with at least a second peptide fragment derived from CMV. The invention also concerns a nucleotide sequence coding for such a protein, or a pharmaceutical composition containing them. It further concerns its use as medicine and a method for preparing the protein.

14 Claims, 7 Drawing Sheets

FIG_6

FIG. 7

SEQUENCE LISTING

```
<160> NUMBER OF SEQ ID NOS:  9

<210> SEQ ID NO 1
<211> LENGTH: 32
<212> TYPE: DNA
<213> ORGANISM: Artificial/Unknown
<220> FEATURE:
<221> NAME/KEY: misc_feature
<222> LOCATION: ()..()
<223> OTHER INFORMATION: primer

<400> SEQUENCE: 1
gatccggatc catggagtcc tctgccaaga ga                            32
```

```
<210> SEQ ID NO 2
<211> LENGTH: 33
<212> TYPE: DNA
<213> ORGANISM: Artificial/Unknown
<220> FEATURE:
<221> NAME/KEY: misc_feature
<222> LOCATION: ()..()
<223> OTHER INFORMATION: primer

<400> SEQUENCE: 2
cccggggaat tcctggtcag ccttgcttct agt                                33

<210> SEQ ID NO 3
<211> LENGTH: 33
<212> TYPE: DNA
<213> ORGANISM: Artificial/Unknown
<220> FEATURE:
<221> NAME/KEY: misc_feature
<222> LOCATION: ()..()
<223> OTHER INFORMATION: primer

<400> SEQUENCE: 3
cccggggaat tcatggcatc cgtactgggt ccc                                33

<210> SEQ ID NO 4
<211> LENGTH: 30
<212> TYPE: DNA
<213> ORGANISM: Artificial/Unknown
<220> FEATURE:
<221> NAME/KEY: misc_feature
<222> LOCATION: ()..()
<223> OTHER INFORMATION: primer

<400> SEQUENCE: 4
gaattcggat cctcaacctc ggtgctrmgg                                    30

<210> SEQ ID NO 5
<211> LENGTH: 20
<212> TYPE: PRT
<213> ORGANISM: Human cytomegalovirus

<400> SEQUENCE: 5

Val Arg Val Asp Met Val Arg His Arg Ile Lys Glu His Met Leu Lys
1               5                   10                  15

Lys Tyr Thr Gln
            20

<210> SEQ ID NO 6
<211> LENGTH: 14
<212> TYPE: PRT
<213> ORGANISM: Human cytomegalovirus

<400> SEQUENCE: 6

Asp Lys Arg Glu Met Trp Met Ala Cys Ile Lys Glu Leu His
1               5                   10

<210> SEQ ID NO 7
<211> LENGTH: 9
<212> TYPE: PRT
<213> ORGANISM: Human cytomegalovirus

<400> SEQUENCE: 7

Ile Pro Ser Ile Asn Val His His Tyr
1               5
```

```
<210> SEQ ID NO 8
<211> LENGTH: 9
<212> TYPE: PRT
<213> ORGANISM: Human cytomegalovirus

<400> SEQUENCE: 8

Asn Leu Val Pro Met Val Ala Thr Val
1               5

<210> SEQ ID NO 9
<211> LENGTH: 15
<212> TYPE: PRT
<213> ORGANISM: Human cytomegalovirus

<400> SEQUENCE: 9

Asn Leu Val Pro Met Val Ala Thr Val Gln Gly Gln Asn Leu Lys
1               5                   10                  15
```

FUSION PROTEIN COMPRISING THE WHOLE OR PART OF THE PP65 PROTEIN OF HUMAN CMV, USEABLE IN PARTICULAR FOR PREPARING A VACCINE

The present invention relates to novel combinations of proteins and to their use as medicament. More particularly, it relates to the preparation of vaccines against CMV.

Human cytomegalovirus (CMV), an enveloped virus with a 230 kbp DNA double strand, is the largest virus of the herpesvirus family. Like the other members of this virus family, it exists in latent form and can undergo repeated reactivation steps which lead to a viremia several years after the initial infection. CMV is widely distributed throughout the world and, while being well tolerated by healthy individuals, it is associated with pathologies which frequently have drastic consequences for the fetus and for immuno-depressed patients (transplant, AIDS and cancer patients) (see Review (1)).

Following a primary infection during pregnancy, the vertical transmission of the virus to the fetus via the placenta leads to complications in the newborn. These are, in particular, sensorial disorders (vision, hearing) and significant mental backwardness which arise during the first few years of the child's life. Infection with CMV is associated with graft rejection in transplant patients (foreign transplants of marrow, kidneys, heart, liver). It constitutes one of the most drastic opportunistic infections in HIV+ patients which, despite antiviral chemotherapy, fall victim to—frequently lethal—pathologies. All these reasons mean that CMV infection raises a substantial public health problem.

The use of unspecific antivirals, such as Ganciclovir* and Foscarnet* during transplantation causes cytotoxicity problems. The secondary effects frequently require a reduced dosage or termination of the treatment, thus posing the risk of the disorder associated with the viral infection recurring. In certain cases, the intravenous injection of high doses of immunoglobulins has reduced the frequency of pneumopathies and rejections. Attempts at adoptive immunotherapy have been developed by injecting, into recipients, marrow of clones of cytotoxic T-cells which are specific for CMV (2).

The development of a subunit vaccine would be of enormous importance to future mothers. In fact, it has been demonstrated that maternal immunity which has been acquired prior to conception could protect the newborn babies from the damage of congenital infection (3). The development of an anti-CMV immunity in transplant patients would be an important factor against the development of infection-associated diseases. Vaccination trials with the attenuated virus of the Towne strain were carried out and are being performed on seronegative volunteers and seronegative transplant patients who have received a transplant from seropositive donors (4). In the majority of the cases, the vaccination has reduced the severity of the diseases associated with viral replication. As the pathogenic activity of such vaccines has not definitively been excluded and where the use of live vaccines might cause severe side effects in immunodeficient individuals, novel approaches using recombinant viral proteins in the presence of adjuvants are being developed.

The importance for public health of developing a vaccine against CMV no longer has to be demonstrated as a result of the problem presented by the congenital infection, which has hitherto been underestimated by the medical community.

The savings made by developing a strategy of preventing diseases linked to CMV infection in risk patients would be substantial. In fact, estimates of the costs associated with the vaccination of an individual and its taking (serological analyses, vaccine, treatment of minor side effects) show that it would be approximately 50 times less than that of the care with which a newborn is provided which is the victim of congenital infection. CMV infection can be observed in ⅔ kidney transplant patients and more often in other transplant patients. Taking into consideration that the infection is associated with complications in approximately ⅓ of these, the annual costs in addition to the transplantation costs are considerable. Despite the impact of drugs such as Ganciclovir*, the injection of gammaglobulins or the transfer of anti-CMV T-clones on the disease, prevention of the primary infection and reactivation in these patients should be a priority. The benefits of an immunization are obvious at the clinical and at the economic level.

The applicant has now found that the combination of CMV protein pp65 or a fragment thereof with another hapten or antigen of CMV allows the immune reaction towards this virus to be potentiated, in particular by stimulating the compartments T CD4+ and CD8+ against the virus.

This is why the present invention relates to a fusion protein, characterized in that it comprises at least part of the cytomegalovirus (or CMV) protein pp65, or of a protein having at least 80% homology with protein pp65, in combination with at least one second peptide fragment derived from CMV.

Protein pp65 is a CMV matrix protein which is internalized in the cells and delivered into the cytosol at the same time as the virion, very shortly after infection.

It can be used whole or in the form of one or more fragments; the peptide fragments which make up the chimeric protein preferably have a length of greater than, or equal to, 9 amino acids and cover different HLA class I restrictions. The applicant has shown that a peptide of protein pp65 of a length greater than 9 amino acids can be internalized by a presenting cell and presented to a CD8+ specific T-line by a class I MHC molecule. The importance of constructions which include these peptides and the protein IE1 for vaccination would be linked to the use of antigens which are capable of entering the presenting cell by a unique endocytosis pathway, simultaneously inducing it to a TCD4+ and TCD8+ response.

The second peptide fragment which is present in the fusion protein is preferably composed of protein IE1 or one of its epitopes, or of a protein having at least 80% homology.

In fact, the polypeptide sequence of IE1, which is a major regulatory protein of the viral cycle, is highly conserved between the different viral strains. Introduction of this protein into a subunit vaccine would allow the induction of memory CD4+ helper T-cells, which are capable of cooperating with the induction of cytotoxic CD8+ T-cells against pp65 and with the production of antibody against the envelope protein gB, subjected to greater variability (cross help). In fact, it has been shown that most of the neutralizing antibodies which are present in the serum of infected individuals were directed against the viral envelope glycoprotein gB (UL55). This is why protein gB was considered to be one of the most important viral antigens for vaccination. A large number of protocols in which recombinant viruses are used (adenovirus, vaccinia, canarypox) have been developed (5, 6, 7).

The problems presented by these vaccines are linked either to the pathogenic character of the live viruses or to the fact that they induce too low antibody titers. An alternative is the use of recombinant antigens which are combined with adjuvants. The combination of glycoprotein gB with the chimeric protein IE1-pp65 into one structure allows its conformation to be maintained, which is indispensable for its immunogenicity, would offer a means for stimulating the T and B compartments of the antiviral response. Moreover, activation of the CD4+ T-cells against IE1, which is mediated by the IE1 peptides in combination with class II MHC molecules being recognized, would allow viral replication in the adjacent cells, which are subjected to the effect of TNFγ and TNFα (8) to be controlled. Naturally, these hypotheses are not intended to limit the scope of the invention.

In particular, use can be made of fragment e4 of CMV protein IE1, or a peptide fragment having at least 80% homology with said fragment e4. e4, or exon 4, which comprises 406 amino acids, is a fragment of protein IE1, which is composed of 491 amino acids.

According to another advantageous aspect of the invention, the fusion protein comprises
  a) the fragment delimited by the amino acid residues 162 and 175 of the sequence of protein IE1, or
  b) a peptide fragment having at least 90% homology with said fragment mentioned under a).

Other epitopes are also suitable for carrying out the invention, such as those mentioned by Davignon et al. (8).

The fusion protein according to the invention can additionally contain a peptide fragment derived from a microorganism other than CMV and/or any polypeptide fragment which allows it to be purified later from Tag-type sequences; these sequences, which are placed upstream or downstream of the protein of interest allow it to be purified or labeled; the use of β-galactosidase, histidine hexamers (His6) or GST may be mentioned as examples. According to a preferred embodiment, the fusion protein comprises a peptide fragment derived from an enzyme with glutathion-S transferase (or GST) activity.

The GST protein will make it easier, in particular, to purify the fusion protein from a complex culture medium.

The invention therefore relates to a chimeric protein GST-IE1-pp65 of 145 kd, which can be prepared in *E. coli*. Its immunogenicity was demonstrated in vitro by the proliferation of IE1-specific CD4+ T-cell-clones and by the lysis of target cells incubated in the presence of a pp65-specific CD8+ T-line. The applicant has shown that the protein in soluble form and its fragments allow the CD4+ and CD8+ T-compartments of the specific cell response to be stimulated in vitro. These results make this protein the reactant of choice for designing a subunit vaccine.

The nucleotide sequences which code for a fusion protein as defined hereinabove are also within the scope of the invention.

The fusion proteins and the corresponding nucleotide sequences can be used as medicament and in particular for the preparation of a vaccine for preventing infections caused by CMV. Such a vaccine will be suitable for inducing an efficient response against a primary infection before the virus has replicated actively.

In accordance with another aspect, the invention relates to a pharmaceutical composition, characterized in that it contains
  a) at least part of the CMV protein pp65 or of a protein having at least 80% homology with protein pp65, in combination with at least one second peptide fragment derived from CMV, or
  b) nucleotide sequences coding for the peptides mentioned under a).

In addition to formulation excipients known to the skilled worker, such as stabilizers, preservatives, antioxidants, adapted to suit the route of administration, in particular an injection, the compositions can contain immunity adjuvants. They can also contain other CMV epitopes. Finally, they can be formulated with systems which improve transport and presentation of the molecules to the target cells.

The proteins can be in the form of various different proteins in the composition; they can also be in the form of a fusion protein as described above; the same applies to the corresponding nucleotide sequences.

In addition, the composition can contain other epitopes, in particular CMV envelope antigens, such as protein gB.

In accordance with yet another aspect, the invention relates to a process for the preparation of a fusion protein, characterized in that the following steps are carried out:
  a) a first DNA sequence which codes for at least a part of the CMV protein pp65 is linked with a second DNA sequence which codes for another polypeptide or protein derived from CMV so as to obtain a recombinant DNA sequence which codes for a fusion protein,
  b) the recombinant DNA sequence is introduced into a construction containing the elements required for its expression, and, if appropriate, sequences which code for other polypeptides,
  c) the construction obtained in b) is introduced into host cells which are subsequently cultured under conditions in which the expression system of the fused DNA is functional, so that the fusion protein is produced in the host cell,
  d) the fusion protein produced in the host cell is recovered and purified.

The host cell which contains a nucleotide sequence coding for a fusion protein, which can be obtained in the process described hereinabove, also comes within the scope of the invention. This host cell can be selected in particular from the group consisting of the bacteria, the viruses, the yeasts and eukaryotic cells, in particular higher eukaryotes.

Other characteristics and advantages of the invention will become obvious from the examples which follow.

Reference will be made in these examples to the following figures.

Lysates of bacteria which have been transformed with plasmids pGEX 2TK (1) and PGEX 2TK/IE1-pp65 (2, 2') were subjected to SDS-PAGE and then to a western blot which is visualized by antibodies against GST (A), against IE1 (B) and against pp65 (C). Pre-stained molecular weight markers (Gibco) have been used.

The cells of clone BeA3G9 were incubated in the presence of irradiated PBMC of the phenotype HLA-DRA8 and GST or GST-IE1-pp65-antigen. Cell proliferation of the clone was determined by the incorporation of [$^3$H]-thymidine, measured in cpm.

The CD8+ T-line "Val" which has been generated with the pp65 peptide N9V was used in a $^{51}$Cr enlargement test in the presence of U373MG cells, either incubated with peptide N9V or with peptide 19Y or infected with CMV Towne (5 moi) for 4 hours and followed by incubation with peptide 19Y. The percentage of specific lysis was calculated as shown in Materials and Methods.

The peptide sequences which correspond to the epitopes presented by HLA-DR8, HLA-A2 and HLA-B35 and their locations are shown SEQ ID NOS:5–9, respectively.

Cells of the line "Val" were used in a $^{51}$Cr enlargement test in the presence of autologous B/EBV lymphocytes which were untreated or pretreated with chloroquine (Materials and Methods) and the peptides and proteins as shown.

Sf9 insect cells were infected for 48 hours with recombinant IE1-pp65 baculoviruses. The cell lysates (1) were centrifuged, and the supernatant (2) was passed through an Ni-agarose column and the eluates were recovered (3, 4). The different fractions were subjected to SDS-PAGE and stained with Coomassie blue.

PBMCs of a CMV+ donor were stimulated with the protein IE1-pp65 (AG) either in soluble form or formulated with SMBV (AG form) or in the absence of antigen (mock). On day 35, the cells are incubated in the presence of protein solutions with or without the protein IE1 (col). The proliferation of the specific anti-IE1 T-cells was determined by measuring the incorporation of tritiated thymidine.

EXAMPLE 1

Production of the Fusion Protein in DH5α Bacteria

Materials and Methods

I-Cloning of IE1 and pp65 cDNAs in PGEX 2TK

I-1 Preparation of the IE1 and pp65 cDNAs

I-1-1 IE1-cDNA

The region of the viral genome containing the sequence which codes for protein IE1 which is located in the Hind III C fragment of the CMV strain Towne was cloned into a plasmid called pRL103. This plasmid was used for transfecting cells of the astrocyte line U373 MG (termed A2 (provided by R. Lafemina, Merck Sharp and Dohme, WestPoint, Pa., USA). These cells were cultured to confluence in RPMI-FCS (RPMI 1640 Glutamax, 1 mM sodium pyruvate, 200 u/ml penicillin, 100 μg/ml streptomycin, 10% decomplemented calf serum). The total RNA of a 3-day culture was prepared following the method of Chomzynski and Sacchi (14). The IEI cDNA was generated by RT-PCR (Kit Super Script, GIBCO BRL) using an aliquot of 5 μg of total RNA, in accordance with the manufacturer's instructions using the primers C1(SEQ ID NO:1): GATCC GGATCCATGGAGTCCTCTGCCAAGAGA and C2(SEQ ID NO:2): CCCGGG GAATTCCTGGTCAGCCTTGCTTCTAGT. BamH1 and EcoR1 sites were introduced into the primers C1 (5'-end of IE1) and C2 (3'-end of IE1), respectively. The PCR product thus obtained (1480 bp) was purified on an S400-HR column (PHARMACIA).

I-1-2 pp65-cDNA

The cells of a human fibroblast line (MRC5, Mérieux) grown in BME supplemented with 10% fetal calf serum (BME/FCS) were infected with CMV (Towne-strain). After a cytopathic effect was observed, the supernatant containing the virus was recovered and heat-inactivated (60° C., 30 minutes). The virus particles were harvested by centrifugation (31,000 g, 4° C., 90 minutes) and the capsids were degraded by treatment with proteinase K (BOEHRINGER) (150 μg) in 250 μl lysis buffer (10 mM TrisCl pH 7.5, 1 mM EDTA, 2% sarcosyl) for 30 minutes at ambient temperature. The viral DNA was extracted with phenol/chloroform and then precipitated with absolute ethanol. The DNA pellet was dried and solubilized in 20 μl of water. A fragment corresponding to the pp65 cDNA was obtained by PCR with an aliquot of 2 μl of viral DNA using the primers C3(SEQ ID NO:3): CCCGGG GAATTCATGGCATCCGTACTGGGTCCC and C4(SEQ ID NO:4): GAATTC GGATCCTCAACCTCGGTGCTTmGG which were complementary to the 5' and 3' ends of the pp65 gene and contained the EcoRI and BamHI sites, respectively. The PCR product (1670 bp) was purified on an S400-HR column (PHARMACIA).

I-2 Construction of the Plasmid pGEX 2TK-IE1-pp65

1-2-1 Purification of the Bam H1- and Eco R1-digested Fragments IE1 and pp65

The IEI and pp65 cDNA fragments were previously cloned into the BamH1 and EcoRI sites of a pUC18 plasmid. Competent DH5α bacteria (GIBCO) were transformed with 5 to 10 ng of a ligation IEI/pUC18 or pp65/pUC18. The recombinant plasmids were digested with BamH1 and EcoR1. The digestion products were separated by agarose gel electrophoresis and extracted from the gel using the "JetSorb/150" kit (GENOMED).

I-2-2 Purification of the IE1-pp65 Fragment

An identical quantity of fragments IE1 and pp65 which have been digested with BamH1 and EcoR1 was incubated in the presence of T4 DNA ligase. The reaction mixture was digested with BamH1. The fragments obtained pp65-pp65 (3340 bp), IE1-pp65 (3150 bp) IE1-IE1 (2960 bp) were separated by agarose gel electrophoresis. The fragment IE1-pp65 was extracted from the gel using the "JetSorb/150" kit (GENOMED).

1-2-3 Cloning of IE1-pp65 into pGEX 2TK

Fragment IE1-pp65 was inserted into the BamH1 site of plasmid PGEX 2TK (PHARMACIA). Clones of the recombinant bacteria were stored at −80° C. in PBS, 3.5% DMSO, until used for protein purification.

II-Production of the Fusion Protein GST-IE1-pp65

An aliquot of bacteria which had been frozen at −80° C. was resuspended in 5 ml of LB medium containing ampicillin (Ap, 50 μg/ml) and cultured for 8 hours at 37° C. The culture, which was diluted with 45 ml of the same medium, was continued for 15 hours and taken up in 500 ml of LB+Ap to an optical density (λ=600 nm) of 1. The production of GST-IE1-pp65 was induced by adding IPTG (100 μM) to the culture medium. The bacteria were harvested by centrifugation after 3 hours of culture at ambient temperature and stored at −80° C.

The bacteria were lysed and the recombinant protein purified by affinity chromatography on a "Sepharose 4-B"

column grafted with glutathion (PHARMACIA) according to the manufacturer's instructions.

The degree of purity of the protein was checked by SDS-PAGE followed by staining with Coomassie blue. The antigenicity of GST-IE1-pp65 was analyzed by western blot using goat antibodies directed against GST (PHARMACIA, dilution 1/400), and mouse antibodies directed against IE1 (supernatant E13 diluted to 1/10, provided by Dr Mazeron, Hal Lariboisière, Paris) and pp65 (NEA 20 diluted to 1/250, DUPONT). Secondary antibodies coupled to RAG/PO, RAM/PO peroxidase (Nordic) were used at 1/500. The proteins were assayed by the method of Bradford using the "Bio-Rad Protein Assay" kit (BIORAD). The recombinant GST protein was produced and purified.

Results and Discussion

Purification of GST-IE1-pp65

Figure 1:
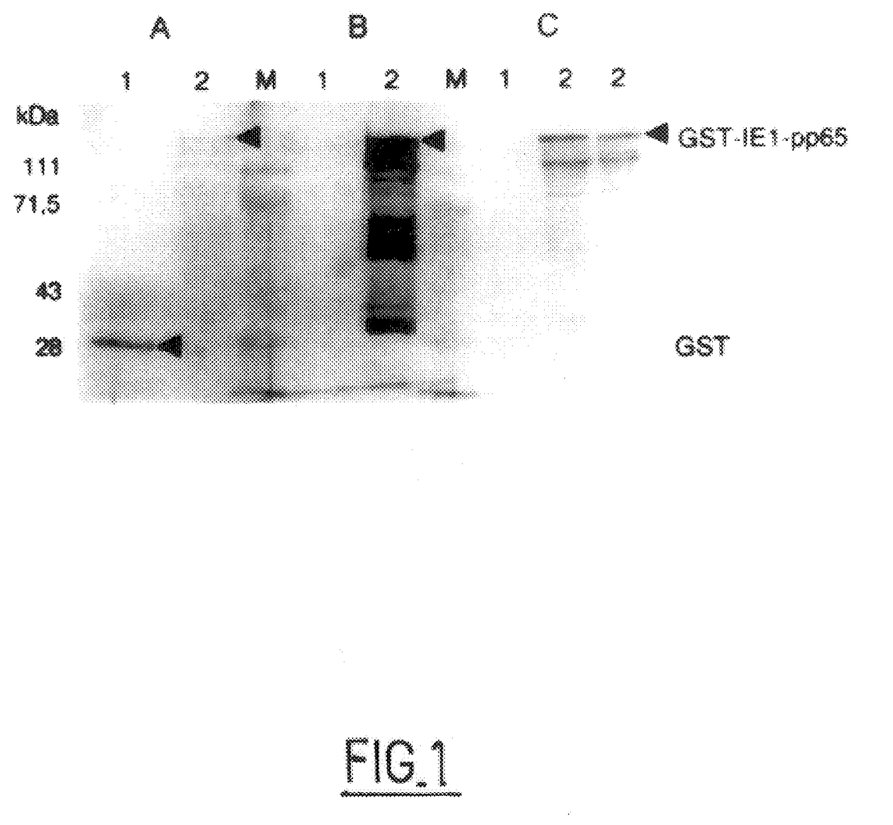
FIG. 1: Western blot analysis of the expression of protein GST-IE1-pp65.
Figure 4:
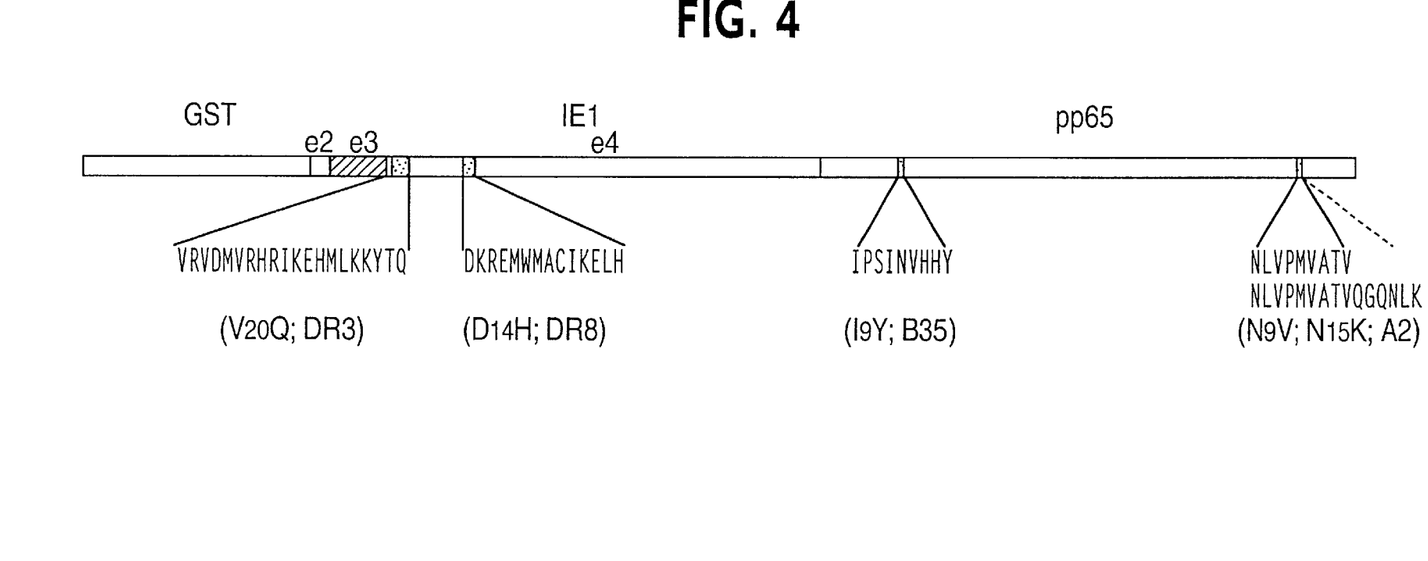
FIG. 4: Schematic representation of recombinant proteins produced in *E. coli*.

On average, we have obtained 1 mg of GST-IE1-pp65 protein purified by glutathion chromatography from a culture of 500 ml of DH5a/pGEX 2TK-IE1-pp65. Analysis by electrophoresis under denaturing conditions followed by a western blot with the antibodies anti-GST, anti-IE1 and anti-pp65 using lysates of recombinant bacteria is shown in FIG. 1. A product corresponding to a theoretical mass of 145 kd was revealed by the three antibodies in the samples prepared from recombinant bacteria. The lower-molecular-weight bands recognized by the antibodies are protein degradation products. These results agree with the production of a protein resulting from the fusion GST-IE1-pp65 in these bacteria (FIG. 4). Trypsin proteolysis of the protein was analyzed by SDS-PAGE and shows that the disappearance of the migration band which corresponds to the whole protein correlated with the appearance of a band of a low molecular weight which corresponds to the generation of peptides. Amongst these fragments, and after analysis of the sequence of the protein, a peptide of 15 aa appears which contains the peptide N9V (see "Materials and Methods" and FIG. 4).

EXAMPLE 2

Materials and Methods

I-Lymphoproliferation Test

Cells ($2 \times 10^4$) of a CD4+ T-clone (BeA3G9) restricted by HLA DR8 and specific for an epitope at position 162–175 of the protein IE1 were incubated in 100 µl of RPMI-SH medium with irradiated (2500 rads) antigen-presenting cells ($1 \times 10^5$ PBMC) of the same HLA-DR phenotype. These cells were incubated with a dilution series of the recombinant protein. On day 3, 1 µCi of [$^3$H]-thymidine (AMERSHAM) was added to each well of the culture. Fifteen hours later, the cell DNA was collected on fiberglass filters (PACKARD), and the incorporation of [$^3$H]-thymidine was measured in a Matrix 9600 gas β counter (PACKARD). Each measurement was carried out in triplicate.

II-Generation of a CD8+ T-line which is Specific for a Peptide of Protein pp65

Peripheral blood leukocytes of CMV-seropositive donors of the haplotype HLA-A2 ($2 \times 10^6$/ml) were cultured in 24-well-plates in RPMI-SH (2 ml). On day 3, 100 U/ml of "Lymphocult-T-LF" (BIOTEST, France) were added. On day 7, the live cells were recovered in the ring of a ficoll gradient. These cells ($5 \times 10^5$/well) were incubated in the presence of autologous stimulator cells ($1.5 \times 10^6$/well) in RPMI-SH (2 ml) supplemented with 10% of "Lymphocult". The stimulator cells ($10 \times 10^6$ cells/ml) were incubated in RPMI in the presence of 30 µg of a peptide presented by HLA-A2 (peptide N9V, FIG. 5, Néosystem, France) for 1 hour at 37° C. and irradiated (2500 rads). The effector cells were restimulated under the same conditions every 7 days. The cytotoxicity of the resulting line "Val" was tested on day 14. The CD8+ phenotype of the line was determined cytofluorimetrically with the monoclonal mouse antibody OKT8.

III-Cytotoxicity Test

III-1 In the Context of CMV Infection

U373MG astrocytoma cells of the haplotype HLA-A2 ($2 \times 10^5$) at 80% confluence in RPMI/FCS were infected with Towne-CMV virus at 5 pfu/cell in 6-well-plates (10 cm2). After infection for 4 hours, the cells were labeled with 100 µCi of $Na_2^{51}CrO_4$ (ICN, France) and washed with RPMI. The autologous effector cells of the CD8+ T-line were incubated with $10^4$ target cells in RPMI/10% FCS (500 µl) for 4 hours at 37° C. Various quantities of effector cells were added to the targets to obtain different effector/target ratios. An alternative treatment was the preincubation overnight at 37° C. of the cells, either with peptide N9V or with a peptide recognized by HLA-B35 (peptide I9Y, FIG. 4, Néosystem, France) at a final concentration of 100 nM.

The rate of spontaneous enlargement was determined by measuring the radioactivity liberated by target cells which were cultured for 4 hours. The percentage of specific lysis was calculated by using the following formula ([measured radioactivity−spontaneous enlargement/total radioactivity−spontaneous enlargement] ×100). The radioactivity is measured on a Cobra-γ-counter (PACKARD). Each measurement is carried out in duplicate.

III-2 In the Presence of the Native or Trypsin— Digested Protein GST-IEI-pp65, With or Without Chloroquine The purified protein GST-IE1-pp65 was demineralized in an ultrafiltration centrifuge with "Centricon 10" filter units (FILTRON), lyophilized and taken up in water and then used in this form or digested with trypsin (TCPK, SIGMA, 200 ng per 900 µg of protein) in a volume of 100 µl of Tris-buffer [100 mM tris-HCl pH 8.0] for 2 hours at 370° C. Aliquots taken before and after digestion were analyzed by SDS-PAGE.

Autologous B-EBV lymphocytes ($1 \times 10^6$) which have previously been washed and irradiated (104 rads) were preincubated either with the antigens (1 µM) for 15 hours at 37° C. in RPMI-FCS medium (0.5 ml) in a 48-well plate or in RPMI-FCS 5%/chloroquine 80 µM (SIGMA) for 30 minutes, before adding the antigens. As an alternative treatment, the cells were preincubated overnight at 37° C. either with peptide N9V or with peptide I9Y at a final concentration of 10 nM. After this incubation had ended, the cells (50,000/ml) were labeled with 100 µCi of $Na_2^{51}CrO_4$ and washed with RPMI. The effector cells of the CD8+ T-line were added under the same conditions as described for the astrocytoma cells.

Results and Discussion

I-Lymphoproliferation of the CD4+ T-clone BeA3G9 in the Presence of GSTIE1-pp65

Figure 2:
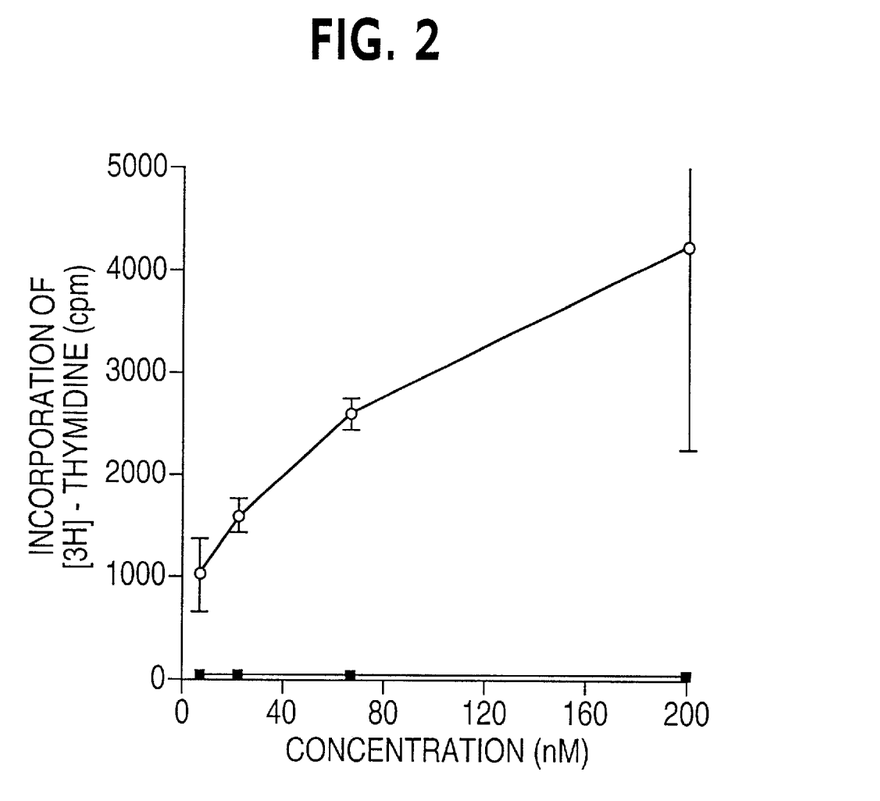
FIG. 2: Protein GST-IE1-pp65 induces a specific proliferation of the CD4+ T-clone BeA3G9 in the presence of PBMC.

FIG. 2 shows the results of the proliferation of the anti-IE1 clone BeA3G9 in the presence of PBMC incubated with the purified recombinant antigen GST-IE1-pp65. The clone proliferated specifically since no incorporation of thymidine was observed in the presence of protein GST. This proliferation was of the same extent as the proliferation obtained with the fusion protein GST-e4 (C-terminal 80% of IE1) or GST-IE1. These results demonstrate that the protein GST-IE1-pp65 was prepared correctly by the HLA-DR8 antigen presenting cells so as to present an IE1 epitope which is recognized by cells of clone BeA3G9.

II-The anti-pp65 CD8+ T-cells of the Line "Val" Lyse Targets Incubated in the Presence of the Trypsin-directed Protein GST-IE1-pp65

II-1 Line "Val" Recognizes a Natural Peptide Generated after Infection With CMV

Figure 3:
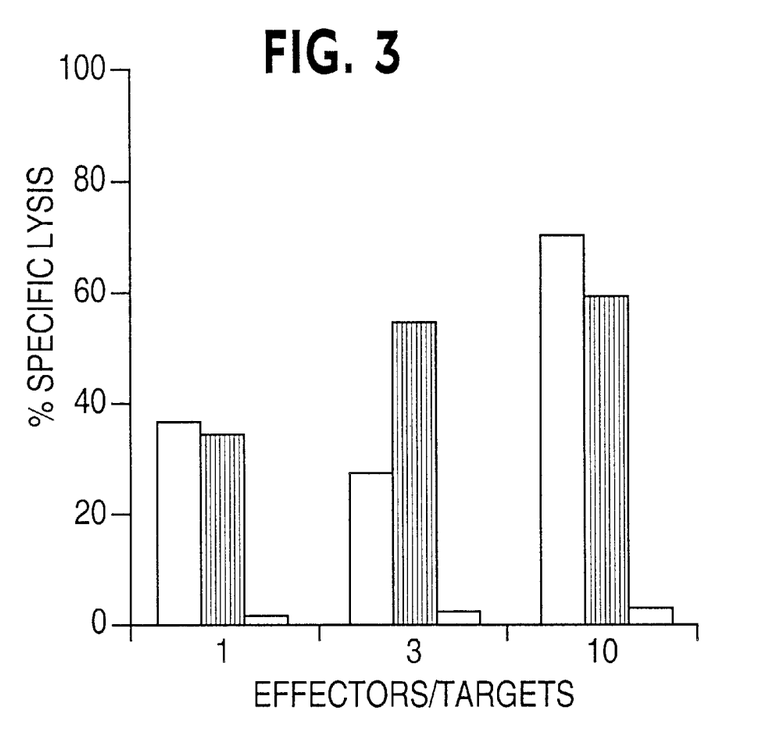
FIG. 3: The anti-pp65 CD8+ T-line "Val" lysis of U373MG astrocytoma cells infected with CMV Towne.

FIG. 3 shows the result of a cytotoxicity test carried out in the context of the infection of U373MG astrocytoma cells of the phenotype HLA-A2. A specific lysis of the targets was observed in the presence of peptide N9V (HLA-A2), while this is virtually zero with peptide I9Y (HLA-B35), which demonstrates that the class I MHC molecules of the phenotype A2 at the surface of the U373MG cells are charged specifically with peptide N9V. When these cells are infected with CMV, a specific lysis of a level equivalent to that obtained with peptide N9V was observed. This suggests that protein pp65, which has been provided by the inoculum, has been delivered into the cytosol and prepared in such a way that a peptide identical to, or of a similar structure to, N9V was generated and presented specifically to the cells of the line "Val".

Figure 5:
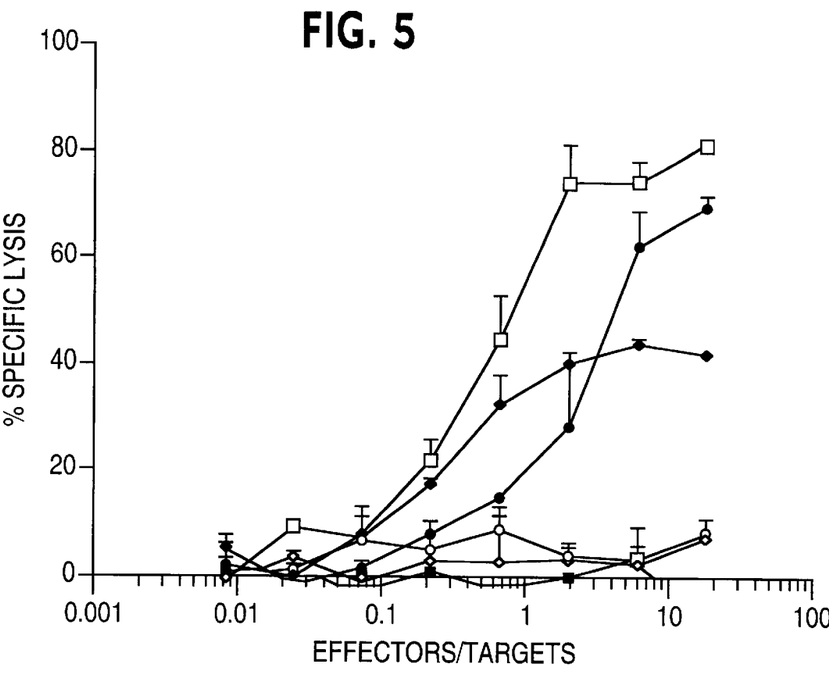
FIG. 5: The anti-pp65 CD8+ T-line "Val" lysis of B/EBV cells incubated in the presence of the trypsin-pretreated protein GST-IE1-pp65.

II-2 B/EBV Lymphocytes Incubated in the Presence of the Trypsin-digested Protein GST-IE1-pp65 are Lysed by the anti-pp65 Line "Val" as an Effect of the Chloroquine-treatment of the Cells The results of an experiment in which the protein GST-IE1-pp65 did not sensitize targets to lysis by line "Val", in contrast to a sample of this same fraction which had been predigested with trypsin, are shown in FIG. 5. When the cells were pretreated with chloroquine and incubated in the presence of the trypsin-digested protein, the targets were not lysed.

Trypsin digestion of the protein generates a peptide of 15 aa, N15K, which contains peptide N9V (FIG. 4). The lysis shown by the targets in the presence of this hydrolysate suggests that peptide N15K is presented to the line "Val". Moreover, chloroquine-pretreatment of the cells shows that this peptide has been internalized by the cells and prepared in an endo-lysosome-type compartment which is sensitive to a pH increase.

EXAMPLE 3

Materials and Methods

Cloning of IE1-pp65 into the Expression Vector "Baculovirus" pAcHLT-B. Cotransfection of Sf9 Insect Cells With the Recombinant Plasmid and Baculovirus DNA The purified fragment IE1-pp65 (Example 1, para. 1-2-2) was inserted into the BglII site of plasmid pAcHLT-B (Pharmingen) which contains a sequence coding for a peptide of 6 histidine residues ($His_6$). The recombinant plasmids were characterized and purified. Sf9 insect cells (ATCC CRL1711) were incubated for 4 hours at 37° C. in the presence of a mixture containing 3 μg of plasmid and 0.5 μg of viral DNA according to the protocol provided by Pharmingen. After 5 days of culture, the protein production was analyzed by a "western blot" using monoclonal antibodies against IE1 (E13, Argene) and against pp65 (NEA20, Biosoft).

Production and Purification of the Protein His6IE1-pp65

The production kinetics of the protein in the infected Sf9 cells were established from days 0 to 5 and analyzed by a "western blot". Lysates of infected cells (lysis buffer: Tris 10 mM, NaCl 130 mM, Triton X-100, NaF 10 mM, NaPi 10 mM, NaPPi 10 mM, pH 7.5, Pharmingen) were applied to an Ni-NTA affinity column (Qiagen) and the protein was eluted with the buffer (NaPO4 50 mM, NaCl 300 mM, glycerol 10%, imidazole 0.5 M, Pharmingen). The degree of purity of the protein was checked by SDS-PAGE and staining with Coomassie blue.

Results

Purification of the Protein His6IE1-pp65

Figure 6:
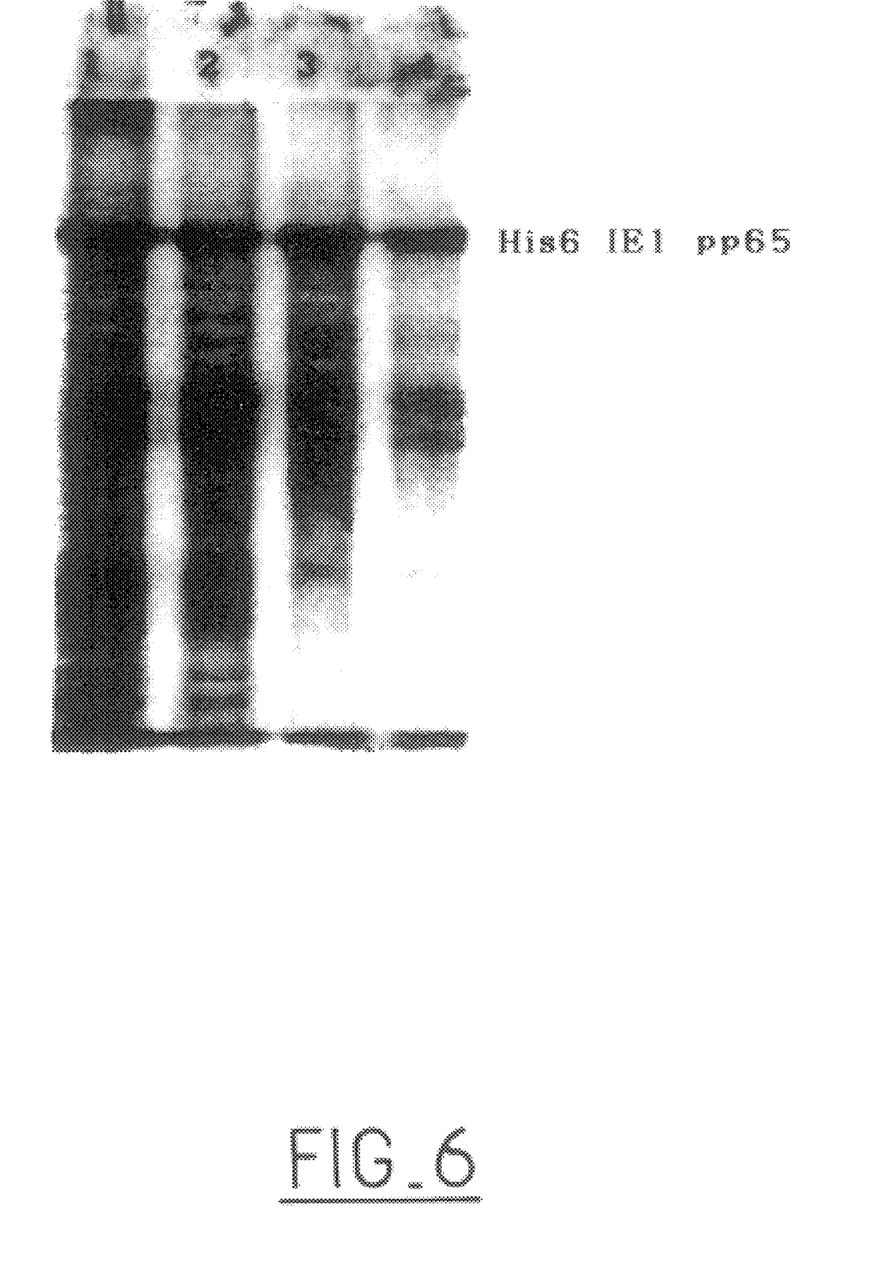
FIG. 6: Analysis of the production of the protein His6-IE1-pp65 by insect cells infected with a recombinant baculovirus.

FIG. 6 shows the SDS-PAGE analysis of the protein $His_6$IE1-pp65 which had been produced by cells infected with recombinant baculoviruses and purified by Ni chromatography. These results demonstrate that the protein constitutes a substantial part of the total cell proteins and is obtained at a higher degree of purity after chromatography.

EXAMPLE 4

Materials and Methods

Induction of the CD4+ T-lines in vitro from PBMC of a CMV+ Donor and Incubated in the Presence of the Chimeric Protein IE1-pp65 Either in Soluble Form or Formulated in SMBV (Supramolecular Biovectors)

The IE1-pp65 formulations were obtained by coincubating for 1 hour at ambient temperature the protein solution (200 nM in PBS with 2.5 mM $Na_2HPO_4/NaH_2PO_4$, 62 mM NaCl, 0.65 mM KCl+10% glycerol) and type L SMBV (1 mg/ml in distilled water) at a protein/biovector weight ratio of 7.7 and a protein/nucleus weight ratio of 10. The L-type SMBV, which is described in WO 94/20078, comprises an external double layer composed of DPPC/cholesterol. Peripheral blood mononuclear cells (PBMC) of a CMV+ donor of the haplotype DR3,13 ("Val") were incubated in 24-well-plates (Falcon) at a density of $4 \times 10^6$ cells in 2 ml of RPMI medium/10% human serum (HS). The soluble or formulated antigen IE1-pp65 was added, and the mixture was incubated for 3 days at 37° C. On day 3, 1 ml of culture medium is replaced by 1 ml of fresh medium supplemented with 10% Lymphocult (100 U/ml, Biotest, France). On day 7, the effector cells are stimulated by incubation with autologous PBMC (at $1.5 \times 10^6$ PBMC per $0.5 \times 10^6$ cells) which had previously been incubated (15 hours) in the presence of either the soluble antigen or the formulated antigen or in the absence of the protein. On day 35, a proliferation test is carried out under the conditions described in Example 2, section Materials and Methods, "Lymphoproliferation test", with the following modifications:

$2 \times 10^4$ effector cells are incubated in the presence of $1 \times 10^5$ allogenic PBMC and of a solution of proteins originating from the lysate of astrocytoma cells U373MG which have been transfected with the IE genes (termed A2) and contain the antigen IE1. A lysate of non-transfected cells (termed AO) was used as negative control.

Results

Figure 7:
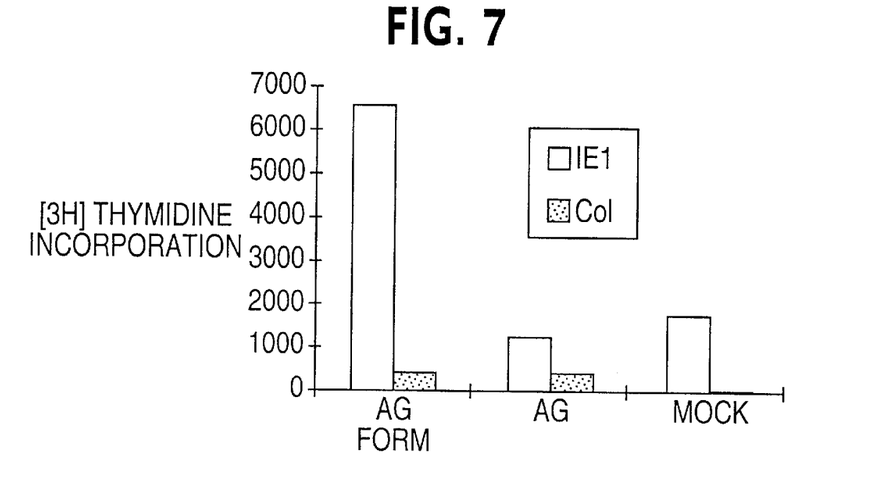
FIG. 7: Induction of anti-IE1 CD4+ T-effectors in a CMV+ donor using formulation SMBV/IE1-pp65.

Induction of the Anti-IE1 CD4+ T-Effectors in a CMV+ Donor from IE1-pp65 Formulations FIG. 7 shows the proliferation of anti-IE1 effectors generated from PBMC of the "Val" donor in the single case where the effectors were induced in the presence of the formulated antigen. This result emphasizes the potentiating effect of the formulation, as has been demonstrated before by Prieur et al (9). These results suggest that under conditions where the frequency of the anti-IE1 CD4+ T-precursors is low as is probably the case with the donor "Val" at the time of removing, the formulation allows those cells which are not stimulated and enlarged when the soluble antigen is used to be stimulated and enlarged. The importance of the use of these formulations for inducing T-effectors in vitro is obvious for the development of transfer protocols, for example for marrow transplantations.

Legends to the Figures

FIG. 2
- ■- GST
- o- GST-IE1-pp65

FIG. 3
- □ N9V
- □ CMV 4h
- □ I9Y

FIG. 5
- ■- I9Y
- □- N9V
- ●- N9V chloroquine
- o- GST-IE1-pp65
- ♦- GST-IE1-pp65, digested
- "- GST-IE1-pp65, digested, chloroquine

FIG. 7

REFERENCES

1. Alford C. A., and Britt W. J.(1990) Cytomegalovirus. In: Virology, Second Edition, (ed. B. N. Fields, and D. M. Knipe et al.), Raven Press Ltd., New York.
2. Riddell, S. R., Watanabe, K. S., Goodrich, J. M., Li, R. C., Agha, M. E., Greenberg, P. D. (1992) Restoration of viral immunity in immunodeficient humans by the adoptive transfer of T cell clones. Sciences 257: 238–241.
3. Fowler, K. B., Stagno, S., Pass, R. F., Britt, W. J., Boll, T. J., Alford, C. A. (1992) The outcome of congenital cytomegalovirus infection in relation to maternal antibody status. N Engl J Med 326: 663–66.
4. Plotkin, S., Higgins, R., Kurtz, J. B., Morris, P. J., Campbell, D. A., Shope, T. C., Spector, S. A., and Dankner, W. M. (1994) Multicenter trial of Towne strain attenuated virus vaccine in seronegative renal transplant recipients. Transplantation 58: 1176–1178.
5. Cranage, M. P., Kouzarides, T., Bankier, A., Satchxell, S.; Weston, K., Tomlinson, P and Barrell, B. Identification of the hyman Cytomegalovirus glycoprotein B gene and induction of neutralizing antibodies via its expression in recombinant vaccinia virus. EMBO J. 1986, 5: 3057–3063.
6. Marshall, G. S., Ricciardi, R. P., Rando, R. F., Puck, J., Ge, R., Plotkin, S. A., and Gonezol, E. An adenovirus recombinant that express the human cytomegalovirus major envelope glycoprotein and induces neutralizing antibodies. J. Infect. Dis. 1990, 162: 1177–1181.
7. Gonczol, E; Berencsi, K., Pincus, S., Endresz; V., Méric, C., Paoletti E., and Plotkin, S. Preclinical evaluation of an ALVAC (canarypox)-human cytomegalovirus glycoprotein B vaccine candidate. Vaccine. 1995, 13: 1080–1085.
8. Davignon J-L, Castanié P., Allan-Yorke J., Gautier N., Clément D., Davrinche C. (1995) Anti-human cytomegalovirus activity of cytokines produced by CD4+ T cell clones specifically activated by IE1 peptides in vitro. J. Virol 70, 2162–2169 (1996).
9. Prieur E, Betbeder D, Niedergang F, Major M, Alcover A, Davignon J-L, Davrinche C. Combination of human cytomegalovirus recombinant immediate-early protein (IE1) with 80 nm cationic biovectors: protection from proteolysis and potentiation of presentation to CD4+ T cell clones in vitro. Vaccine, 1996, 14: 511–520.

---

What is claimed is:

1. A fusion protein, comprising a first peptide fragment having at least 80% homology with CMV protein pp65, in combination with a second peptide fragment having i) at least nine amino acids derived from CMV protein IE1 or one of its epitopes, or ii) at least 80% homology with protein IE1.

2. The fusion protein according to claim 1, wherein the second peptide is derived from fragment e4 of CMV protein IE1, or a peptide fragment having at least 80% homology to said fragment e4.

3. The fusion protein according to claim 1, wherein the second peptide fragment is selected from the group consisting of:
   (a) amino acid residues 162–175 of protein IB1, and
   (b) a peptide fragment having at least 90% homology with fragment (a).

4. A fusion protein according to claim 1, further comprising a third peptide fragment derived from a microorganism other than CMV.

5. A fusion protein according to claim 4, wherein the third peptide fragment is upstream or downstream of the fused first and second peptide fragments.

6. A fusion protein according to claim 4, further comprising a Tag-sequence.

7. A fusion protein according to claim 6, wherein the Tag-sequence is selected from the group consisting of a fragment of glutathion-S transferase (GST), an enzyme with GST activity, a fragment of β-galactosidase, and a histamine heximer.

8. A fusion protein according to claim 6, comprising GST-IE1-pp65.

9. A fusion protein of claim 8, having molecular weight of 145 kd.

10. A non-naturally occurring polynucleotide molecule encoding a fusion protein according to claim 1.

11. A non-naturally occurring polynucleotide molecule encoding a fusion protein according to claim 3.

12. A non-naturally occurring polynucleotide molecule encoding a fusion protein according to claim 6.

13. A non-naturally occurring polynucleotide molecule encoding a fusion protein according to claim 8.

14. A method of for activating IE1-specific CD4+ or pp65-specific CD8+ T-cells in vitro comprising administering an effective amount of the fusion protein of claim 1 to the IE1-specific CD4+ or pp65-specific CD8+ T-cells.

* * * * *